(12) United States Patent
Chang et al.

(10) Patent No.: US 8,772,344 B2
(45) Date of Patent: Jul. 8, 2014

(54) PHARMACEUTICAL COMPOSITION FOR INHIBITING OSTEOCLAST GROWTH

(75) Inventors: Deh-Ming Chang, Taipei (TW); Hsu-Shan Huang, Taipei (TW)

(73) Assignee: National Defense Medical Center, Taipei (TW)

( * ) Notice: Subject to any disclaimer, the term of this patent is extended or adjusted under 35 U.S.C. 154(b) by 272 days.

(21) Appl. No.: 13/180,253

(22) Filed: Jul. 11, 2011

(65) Prior Publication Data

US 2012/0232105 A1 Sep. 13, 2012

(30) Foreign Application Priority Data

Mar. 11, 2011 (TW) .............................. 100108249 A (51) Int. Cl.
*A61K 31/167* (2006.01)
*A61K 31/505* (2006.01)
*A61K 31/426* (2006.01)
*A61K 31/18* (2006.01)

(52) U.S. Cl.
CPC ............. *A61K 31/167* (2013.01); *A61K 31/505* (2013.01); *A61K 31/426* (2013.01); *A61K 31/18* (2013.01)
USPC ............ 514/622; 514/603; 514/370; 514/275

(58) Field of Classification Search
CPC .................................................. A61K 31/167
USPC ....................................................... 514/622
See application file for complete search history.

(56) References Cited

U.S. PATENT DOCUMENTS 5,905,090 A * 5/1999 Bertolini et al. .............. 514/522

FOREIGN PATENT DOCUMENTS

WO WO 2006/132583 * 12/2006

OTHER PUBLICATIONS

Brown et al. Bioorganic & Medicinal Chemistry, 2008, vol. 16, pp. 8760-8764.*

* cited by examiner

*Primary Examiner* — James D Anderson
(74) *Attorney, Agent, or Firm* — WPAT, P.C.; Anthony King (57) ABSTRACT

A pharmaceutical composition for inhibiting osteoclast growth is disclosed in the present invention. The pharmaceutical composition includes a compound represented by a formula (I), and a pharmaceutically acceptable salt and carrier:

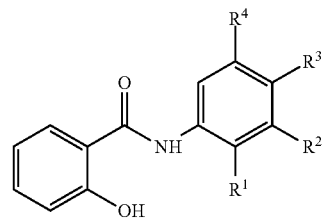

wherein $R^1$, $R^2$, $R^3$, $R^4$ can be one selected from a group consisting of hydrogen, halogen, $C_1$~$C_{10}$ alkyl group, $C_2$~$C_{10}$ alkynyl group, amino group, haloalkyl group and sulfonamide group.

6 Claims, 9 Drawing Sheets

PHARMACEUTICAL COMPOSITION FOR INHIBITING OSTEOCLAST GROWTH

CROSS-REFERENCE TO RELATED APPLICATIONS

This Non-provisional application claims priority under 35 U.S.C. §119(a) on Patent Application No(s). 100108249 filed in Taiwan, Republic of China, Mar. 11, 2011 the entire contents of which are hereby incorporated by reference.

BACKGROUND OF THE INVENTION

1. Field of the Invention

This invention relates to a pharmaceutical composition for inhibiting osteoclast growth and, more particularly, to a plurality of the pharmaceutical composition comprising benzamide derivatives.

2. Description of the Related Art

The human bone is a highly dynamic organ that maintains its homeostasis through a delicate balance between bone formation and resorption, mediated by the bone-forming osteoblasts and the bone eroding osteoclasts. This balance between these two cells types results in bone remodeling, and this continues unless critical changes in the balance occur. Increased osteoclast activity induces thinning and trabecular bone erosion, resulting in many diseases of Bone, such as osteoporosis, periodontitis and osteoarthritis.

The osteoblasts arose from mesenchymal cells are responsible for the formation of bond. The specific transcription factor of osteoblasts, such as Runx2/cbfa1 (runt-related transcription factor-2) and osterix, can regulate the mesenchymal cells to precursor cell and introduce the formation of type I collagen, alkaline phophatase (ALP) and bone sailoprotein. The osteocalcin (OCN) and osteopontin formed in the later period which can promote the precursor cell to differentiate and process mineralization can create the star-shaped osteocytes forming the bone in bone base. In addition, the precursor cell can also divide to lining cells in flat shape and less organelle which are covered on the surface of the bond and introduce to modify the bone remodeling.

The osteoclasts arose from hematopoietic precursor cells. Furthermore, the Macrophage-Colony Stimulating Factor (M-CSF) and the Receptor Activator of Nuclear factor Kappa B Lignad (RANKL) secreted by the osteoblasts will combine with c-Fms and RANK on the cell membrane of the precursor cell, respectively, for increasing the secretions of tartrate-resistant acid phosphatase (TRAP), perform and appearance integrin b3 . . . etc. The changes of the activities of the proteins and the shape of the cell will improve the movement of the osteoclasts and the attaching ability of the osteoclasts on the bond surface. On the other hand, the presence of the enzyme, such as cathepsin K matrix metalloproteinase-9(MMP-9), dendritic cell-specific transmembrane protein (DC-STAMP), ATPase $H^+$ transporting lysosomal V0 subunit D2 (ATP6V0D2), involved in the cell combination and the bone eroding will be presented, so as to introduce the precursor cell differentiating to the big and fully grown (radius of 20 to 100 mm) multi-nuclei cell including 4 to 20 cell nucleuses and the multi-nuclei cell will result in the bone eroding. The osteoblasts not only can secrete M-CSF and RANKL to promote the growing and differentiating of the osteoclasts, but also secrete osteoprotegerin (OPG). OPG will block the formation of the osteoclasts by combining with RANKL to prevent that RANKL combine with RANK. Restraining the formation of the osteoclasts will decrease the happening of the bone eroding. Moreover, OPG also involve the apoptosis of the osteoclasts.

BRIEF SUMMARY OF THE INVENTION

According to the abovementioned, the present invention provides a plurality of pharmaceutical compositions comprising benzamide derivatives for inhibiting osteoclast growth and preventing osteoporosis.

In accordance with the purpose of the present invention, the pharmaceutical composition includes a compound represented by a formula (I) and a pharmaceutically acceptable salt and carrier:

I wherein $R^1$, $R^2$, $R^3$, $R^4$ can be one selected from a group consisting of hydrogen, halogen, $C_1$~$C_{10}$ alkyl group, $C_2$~$C_{10}$ alkynyl group, amino group, haloalkyl group and sulfonamide group.

Preferably, $R^1$, $R^2$, $R^3$, $R^4$ can be fluorine, chlorine, bromine or iodine.

Preferably, $R^1$, $R^2$, $R^3$, $R^4$ can be hydrogen, a methyl group, an ethyl group, a propyl group, a butyl group, a pentyl group, a hexyl group, a heptyl group, an octyl group, an nonyl group or a decyl group, and the $C_1$~$C_{10}$ alkyl group can be a straight alkyl group, a branched alkyl group, a tautomers or a stereoisomerism.

Preferably, $R^1$, $R^2$, $R^3$, $R^4$ can be hydrogen, a 2-trifluoromethyl group, a 3-trifluoromethyl group, a 4-trifluoromethyl group, a 2-trichloromethyl group, a 3-trichloromethyl group, a 4-trichloromethyl group, a 2-tribromomethyl group, a 3-tribromomethyl group, a 4-tribromomethyl group, a 2-triiodomethyl group, a 3-triiodomethyl group, a 4-triiodomethyl group, a 2-fluoromethyl group, a 2-fluoroethyl group, a 2-fluoropropyl group, a 2-difluoromethyl group, a 3,5-difluoro group, a 2,3-difluoro group, a 3,4-difluoro group, a 2,4-difluoro group, a 2,3,4-trifluoro group, a 3,4,5-trifluoro group, a 2-fluoro 4-chloro group or a 3-chloro 4-fluoro group.

Preferably, $R^1$, $R^2$, $R^3$, $R^4$ can be hydrogen, a 2-ethynyl group, a 3-ethynyl group, a 4-ethynyl group, a 2-propynyl group, a 3-propynyl group, a 4-propynyl group, a 2-butynyl group, a 3-butynyl group, a 4-butynyl group, a 2-pentynyl group, a 3-pentynyl group, a 4-pentynyl group, a 2-hexynyl group, a 3-hexynyl group, a 4-hexynyl group, a 2-heptynyl group, a 3-heptynyl group, a 4-heptynyl group, a 2-octynyl group, a 3-octynyl group, a 4-octynyl group, a 2-nonynyl group, a 3-nonynyl group, a 4-nonynyl group, a 2-decynyl group, a 3-decynyl group or a 4-decynyl group.

Preferably, $R^3$ can be a 4-sulfonamide group, a thiazolsulfonamide group, an isothiazolsulfonamide group or a methylpyridinesulfonamide group.

Preferably, $R^2$, $R^3$ are both fluoro groups, $R^1$, $R^4$ are both hydrogen, and the pharmaceutical composition comprises N-(3,4-difluorophenyl)-2-hydroxybenzamide and a pharmaceutically acceptable salt and carrier.

Preferably, $R^1$ is a fluoro group, $R^3$ is a chloro group, and the pharmaceutical composition comprises N-(4-chloro-2-fluorophenyl)-2-hydroxybenzamide and a pharmaceutically acceptable salt and carrier.

Preferably, one of $R^2$ and $R^4$ is a trifluoro group, the other one of $R^2$ and $R^4$, $R^1$ and $R^3$ are both hydrogen, and the pharmaceutical composition comprises 2-hydroxy-N-[3-(trifluoromethyl)phenyl]benzamide and a pharmaceutically acceptable salt and carrier.

Preferably, one of $R^2$ and $R^4$ is an ethynyl group, the other one of $R^2$ and $R^4$, $R^1$ and $R^3$ are both hydrogen, and the pharmaceutical composition comprises N-(3-ethynylphenyl)-2-hydroxybenzamide and a pharmaceutically acceptable salt and carrier.

Preferably, the carrier is an excipient, a diluent, a thickener, a filler, a binder, a disintegrant, a lubricant, a oleaginous base, an non-oleaginous base, a surfactant, a suspending agent, a coagulant, an auxiliary agent, a preservative, an anti-oxidant, a stabilizer, a colorant or a Flavoring.

Preferably, the excipient comprises microcrystalline cellulose, polyvinylpyrrolidone, corn starch, modified starches, sodium starch glycolate, resin, gelatinized starches, carbohydrate, polyethylene glycol, polyvinyl alcohol, hydroxypropyl cellulose, methylcellulose, hydroxymethyl cellulose or hydroxypropyl methylcellulose.

Preferably, the pharmaceutically acceptable salt are a physiologically acceptable with inorganic/organic acid or base.

Preferably, the pharmaceutical composition is a powder, a grain, a liquid, a colloid or a paste.

Preferably, the pharmaceutical composition can be administered through oral administration, transcutaneous administration, injection administration or inhalation administration.

Preferably, the pharmaceutical composition is used for decreasing bone resorption, thus to prevent osteoporosis.

This invention will process pharmacological activity assay of a plurality of the pharmaceutical composition comprising benzamide derivatives, and decrease bone resorption to prevent osteoporosis, inhibiting bone resorption and treating osteoporosis with a series embodiments as follows.

DETAILED DESCRIPTION OF THE INVENTION

The present invention provides a plurality of pharmaceutical compositions comprising benzamide derivatives. The abovementioned pharmaceutical compositions can be used for inhibiting osteoclast growth and decreasing bone resorption to prevent osteoporosis.

The pharmaceutical composition includes a compound represented by a formula (I) and a pharmaceutically acceptable salt and carrier:

wherein $R^1$, $R^2$, $R^3$, $R^4$ can be one selected from a group consisting of hydrogen, halogen, $C_1$~$C_{10}$ alkyl group, $C_2$~$C_{10}$ alkynyl group, amino group, haloalkyl group and sulfonamide group.

In a preferred embodiment, the haloalkyl group can be a 2-trifluoromethyl group, a 3-trifluoromethyl group, a 4-trifluoromethyl group, a 2-trichloromethyl group, a 3-trichloromethyl group, a 4-trichloromethyl group, a 2-tribromomethyl group, a 3-tribromomethyl group, a 4-tribromomethyl group, a 2-triiodomethyl group, a 3-triiodomethyl group, a 4-triiodomethyl group, a 2-fluoromethyl group, a 2-fluoroethyl group, a 2-fluoropropyl group, a 2-difluoromethyl group.

The $C_2$~$C_{10}$ alkynyl group can be a 2-ethynyl group, a 3-ethynyl group, a 4-ethynyl group, a 2-propynyl group, a 3-propynyl group, a 4-propynyl group, a 2-butynyl group, a 3-butynyl group, a 4-butynyl group, a 2-pentynyl group, a 3-pentynyl group, a 4-pentynyl group, a 2-hexynyl group, a 3-hexynyl group, a 4-hexynyl group, a 2-heptynyl group, a 3-heptynyl group, a 4-heptynyl group, a 2-octynyl group, a 3-octynyl group, a 4-octynyl group, a 2-nonynyl group, a 3-nonynyl group, a 4-nonynyl group, a 2-decynyl group, a 3-decynyl group or a 4-decynyl group.

The sulfonamide group is represented by a formula (II):

Wherein $R^5$ can be hydrogen, a thiazol group, a isothiazol group or a piperidine group, and hydrogen of the thiazol group or the piperidine group being partially substituted by other substituent, for example, a $C_1$~$C_{10}$ alkyl group.

In the preferred embodiment, the carrier is an excipient, a diluent, a thickener, a filler, a binder, a disintegrant, a lubricant, a oleaginous base, an non-oleaginous base, a surfactant, a suspending agent, a coagulant, an auxiliary agent, a preservative, an anti-oxidant, a stabilizer, a colorant or a Flavoring.

In the preferred embodiment, the excipient comprises microcrystalline cellulose, polyvinylpyrrolidone, corn starch, modified starches, sodium starch glycolate, resin, gelatinized starches, carbohydrate, polyethylene glycol, polyvinyl alcohol, hydroxypropyl cellulose, methylcellulose, hydroxymethyl cellulose or hydroxypropyl methylcellulose. However, the present invention is not limited thereto.

In the preferred embodiment, the pharmaceutically acceptable salt are a physiologically acceptable with inorganic/organic acid or base. In the preferred embodiment, the pharmaceutical composition is a powder, a grain, a liquid, a colloid or a paste, and the pharmaceutical composition can be administered through oral administration, transcutaneous administration, injection administration or inhalation administration.

According to the above mentioned compound, a plurality of the benzamide derivatives manufactured by cooperating the compound A as the reactant with the compound B comprising the abovedmentioned substituents will be disclosed with a series embodiments and table 1 as follows.

First, please refer to the table 1, the table presents the structural formula of the pharmaceutical compositions for inhibiting osteoclast growth manufactured according to the present invention. The pharmaceutical compositions are manufactured by reacting the compound A (salicylic acid) with nine kinds of the compound B, separately.

TABLE 1

[Compound A: salicylic acid structure]

| Compound B | Number | Product |
|---|---|---|
| 3-(trifluoromethyl)aniline | 1 | N-(3-(trifluoromethyl)phenyl)salicylamide |
| 4-ethynylaniline | 2 | N-(4-ethynylphenyl)salicylamide |
| 3-ethynylaniline | 3 | N-(3-ethynylphenyl)salicylamide |
| 3-chloro-4-fluoroaniline | 4 | N-(3-chloro-4-fluorophenyl)salicylamide |
| 3,4-difluoroaniline | 5 | N-(3,4-difluorophenyl)salicylamide |

TABLE 1-continued

| Compound B | Number | Compound A |
|---|---|---|
|  | 6 |  |
|  | 7 |  |
|  | 8 |  |
|  | 9 |  |

(Compound A shown at top of table: )

According to the structural formula of the nine compound listed in the table 1, wherein the compound No. 1, 3, 5 and 6 have the most significant effect for inhibiting osteoclast growth, and the results are listed as follows. First, the pharmaceutical composition comprises 2-hydroxy-N-[3-(trifluoromethyl)phenyl]benzamide and a pharmaceutically acceptable salt and carrier (the compound No. 1) when $R^2$ is a trifluoro group and $R^1$, $R^3$ and $R^4$ are both hydrogen. And then, the pharmaceutical composition comprises N-(3-ethynylphenyl)-2-hydroxybenzamide and a pharmaceutically acceptable salt and carrier (the compound No. 3) when $R^2$ is an ethynyl group and $R^1$, $R^3$ and $R^4$ are both hydrogen. And further, the pharmaceutical composition comprises N-(3,4-difluorophenyl)-2-hydroxybenzamide and a pharmaceutically acceptable salt and carrier (the compound No. 5) when $R^2$, $R^3$ are both fluoro groups, and $R^1$, $R^4$ are both hydrogen. Finally, the pharmaceutical composition comprises N-(4-chloro-2-fluorophenyl)-2-hydroxybenzamide and a pharmaceutically acceptable salt and carrier (the compound No. 6) when $R^1$ is a fluoro group, and $R^3$ is a chloro group.

The present invention further provides the manufacture methods of the compound No. 1, 3, 5 and 6. However, the present invention will not limit to any dose, ratio or reaction time.

Embodiment 1

2-hydroxy-N-[3-(trifluoromethyl)phenyl]benzamide, No. 1

Cf

The compound A (0.276 g, 2 mmol) is dissolved in 10 mL of dichloromethane, 1-Hydroxybenzotriazole monohydrate (0.270 g, 2 mmol) and N-Ethyl-N'-(3-dimethylaminopropyl)carbodiimide hydrochloride (0.383 g, 2 mmol) are then added thereinto. The abovementioned solution is added by 3-(Trifluoromethyl)aniline (the compound B, 0.354 ml, 2.2 mmol) and stirred under room temperature for 72 hours. The mixture is treated by using a rotary evaporator. After extracting by dichloromethane and removing water by magnesium sulphate, the precipitate is collected and washed by hot ethanol, so as to obtain the white compound No. 1.

The compound No. 1 has the following characteristics: $C_{14}H_{10}F_3NO_2$ Yield: 17.43%. mp: 169° C. MS (ESI-TOF): 281.4. 1H-NMR (300 MHz, DMSO) δ (ppm)) 6.835-7.004 (m, 2H, H-1,3), 7.374-7.536 (m, 2H, H-6,7), 7.551-7.623 (m, 1H, H-2,5), 7.891-7.984 (m, 2H, H-4), 8.212 (s, 1H, H-8), 10.590 (s, 1H, NH), 11.519 (s, 1H, OH)

Embodiment 2

N-(3-ethynylphenyl)-2-hydroxybenzamide, No. 3

Ci

The compound A (0.276 g, 2 mmol) is dissolved in 10 mL of dichloromethane, 1-Hydroxybenzotriazole Hydroxybenzotriazole monohydrate monohydrate (0.270 g, 2 mmol) and N-Ethyl-N'-(3-dimethylaminopropyl)carbodiimide hydrochloride (0.383 g, 2 mmol) are then added thereinto. The abovementioned solution is added by 3-Ethynylanlilne (the compound B, 0.258 ml, 2.2 mmol) and stirred under room temperature for 66 hours. The mixture is treated by using a rotary evaporator. After extracting by dichloromethane and removing water by magnesium sulphate, the precipitate is collected and washed by hot ethanol, so as to obtain the purple compound No. 3.

The compound No. 3 has the following characteristics: $C_{15}H_{11}NO_2$. Yield: 24.04%. mp: 175-176° C. MS (ESI-TOF): 236.8. 1H-NMR (300 MHz, DMSO) δ (ppm): 4.184 (s, 1H, CH), 6.930-6.994 (m, 2H, H-1,3), 7.218-7.252 (m, 1H, H-6,7), 7.349-7.459 (m, 2H, H-2,5), 7.641-7.894 (m, 1H, H-8), 7.900-7.936 (m, 2H, H-4), 10.412 (s, 1H, NH), 11.612 (s, 1H, OH).

Embodiment 3

N-(3,4-difluorophenyl)-2-hydroxybenzamide, No. 5

Cl

The compound A (0.276 g, 2 mmol) is dissolved in 10 mL of dichloromethane, 1-Hydroxybenzotriazole monohydrate (0.270 g, 2 mmol) and N-Ethyl-N'-(3-dimethylaminopropyl)carbodiimide hydrochloride (0.383 g, 2 mmol) are then added thereinto. The abovementioned solution is added by 3,4-Difluoroaniline (the compound B, 0.28 ml, 2.2 mmol) and stirred under room temperature for 72 hours. The mixture is treated by using a rotary evaporator. After extracting by dichloromethane and removing water by magnesium sulphate, the precipitate is collected and washed by hot ethanol, so as to obtain the green compound No. 5.

The compound No. 5 has the following characteristics: $C_{13}H_9F_2NO_2$. Yield 36.54%. mp: 191-192° C. MS (ESI-TOF): 249.2. 1H-NMR (300 MHz, DMSO) δ (ppm): 6.928-

6.997 (m, 2H, H-1,3), 7.392-7.492 (m, 3H, H-2,5,6), 7.854-7.931 (m, 2H, H-4,7), 10.478 (s, 1H, NH), 11.563 (s, 1H, OH).

Embodiment 4

N-(4-chloro-2-fluorophenyl)-2-hydroxybenzamide, No. 6

The compound A (0.276 g, 2 mmol) is dissolved in 10 mL of dichloromethane, 1-Hydroxybenzotriazole monohydrate (0.270 g, 2 mmol) and N-Ethyl-N'-(3-dimethylaminopropyl) carbodiimide hydrochloride (0.383 g, 2 mmol) are then added thereinto. The abovementioned solution is added by 4-Chloro-2-fluoroaniline (the compound B, 0.32 ml, 2.2 mmol) and stirred under room temperature for 72 hours. The mixture is treated by using a rotary evaporator. After extracting by dichloromethane and removing water by magnesium sulphate, the precipitate is collected and washed by hot ethanol, so as to obtain the compound No. 6 (skin color).

The compound No. 6 has the following characteristics: $C_{13}H_9ClFNO_2$. Yield: 14.53%. mp: 184-185° C. MS (ESI-TOF): 265.4. 1H-NMR (300 MHz, DMSO) δ (ppm)) 6.962-7.025 (m, 2H, H-1), 7.292-7.299 (m, 1H, H-3), 7.348-7.425 (m, 1H, H-6), 7.545 (dd, J=2.4 Hz, 1H, H-2), 7.996 (dd, J=1.5, 1.8 Hz, 1H, H-5), 8.244 (t, J=8.7 Hz, 1H, H-7), 10.711 (s, 1H, NH), 11.893 (s, 1H, OH).

In order to prove that the compound No. 1, 3, 5 and 6 contained the benzamide derivatives represented by formula (I) can effectively inhibit osteoclast growth, the compounds No. 1, 3, 5 and 6 manufactured by the method discloses in the present invention will process a series of tests as follows.

Embodiment 5

Osteoclast Formation

Bone marrow cells (BMCs) from DBA/1J mice were obtained for osteoclast progenitor cell preparation. The BMCs were isolated from the tibias and femurs of 8-wk-old male mice by flushing the bone marrow cavity with PBS. The cells were then centrifuged at 1000 g for 10 min and exposed to 5 ml of hypotonic ACK buffer (0.15 mM NH4Cl, 1 mM KCO3, and 0.1 mM EDTA, (pH 7.4)) at room temperature for 5 mM to remove the red blood cells. They were incubated with α-MEM (Gibco BRL) containing penicillin (100 U/ml), streptomycin (100 μg/ml) and 10% heat-inactivated FBS for 12 hr to separate the floating and adherent cells. The floating cells were collected, suspended in α-MEM, counted, seeded onto a 96-well plate at $4\times10^4$ cells/well, and cultured in α-MEM in the presence of 30 ng/ml M-CSF for 3 days to form macrophage-like osteoclast precursor cells. After the floating cells, including the lymphocytes, were removed by aspiration, the adherent osteoclast precursors were co-cultured with activated lymphocytes in the presence of 30 ng/ml M-CSF and 100 ng/ml RANKL as well as compound No. 1, 3, 5 and 6 (10, 15, 20 μM) for 5 days to generate osteoclasts. On day 3, the medium was replaced with fresh medium containing M-CSF, RANKL and P. amboinicus.

Embodiment 6

Cell Culture of Murine RAW264.7

Murine RAW264.7 (murine leukemic monocyte/macrophage), a type of osteoclast progenitor cells. The murine monocyte/macrophage cell line RAW264.7 was cultured with DMEM (Gibco BRL) containing 10% heat-inactivated FBS, penicillin (100 U/ml), and streptomycin (100 μg/ml). All cells were grown in a humidified atmosphere containing 5% $CO^2$ at 37. To induce osteoclast differentiation, RAW264.7 cells were suspended in α-MEM containing 10% FBS, 2 mM L-glutamate, 100 U/ml penicillin, and 100 μg/ml streptomycin, seeded at $10^4$ cells/dish in a 96-well plate and cultured with 100 ng/ml soluble RANKL for 5 days. The medium was changed on day 3.

Embodiment 7

Tartrate-Resistant Acid Phosphatase (TRAP) Staining and Activity

TRAP staining was performed as described Han et al. 2007. Briefly, cells were washed with PBS and fixed with 3.7% formaldehyde for 30 min. After washing with PBS, cells were incubated at 37 in a humid and light-protected incubator for 1 hr in the reaction mixture of the Leukocyte Acid Phosphatase Assay kit (Cat. 387, Sigma), as directed by the manufacturer. Cells were washed three times with distilled water and TRAP-positive multinucleated cells containing five or more nuclei were counted under a light microscope. To measure TRAP activity, cells were lysed in 150λ of 0.2% Triton X-100 in PBS, RT for 15 min and then incubated with 100λ of phosphatase substrate solution kit (Cat. CS0740, Sigma) at 37 for 30 min. After incubation, the enzyme reaction mixture was transferred to another plate and the reaction was stopped with 100λ of 0.5N NaOH. Absorbance was measured at 405 nm in a ELISA plate reader, and activity calculated from standard curve generated using p-nitrophenol standards. TRAP activity was normalized to total protein (determined by the BCA assay (Cat. 23225, PIERCE)) as well as to total number of nuclei counted after TRAP and hematoxylin staining of a second, identical 96-well plate run in conjunction with that used for the TRAP assay.

Figure 1A:
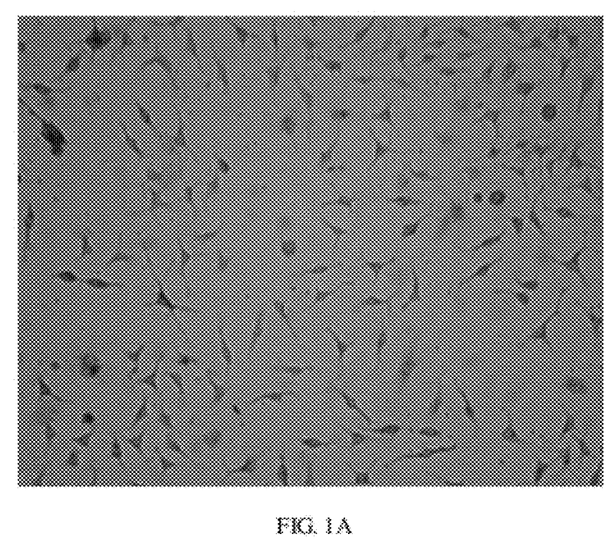
FIG. 1A is a diagram showing the results of observing bone marrow-derived macrophages in a plate treated with M-CSF.
Figure 1B:
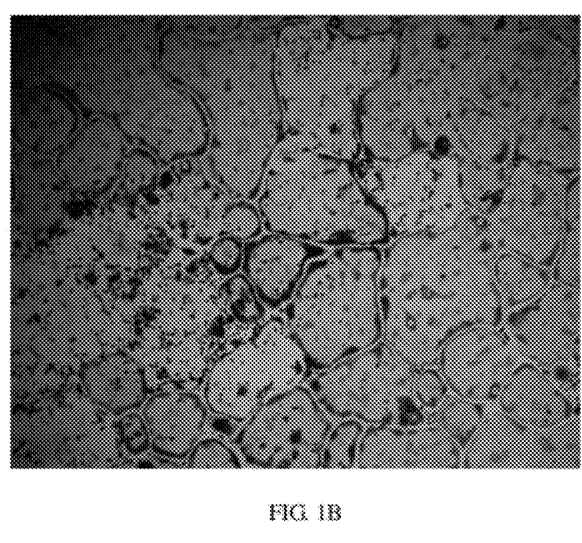
FIG. 1B is a schematic diagram showing the results of observing bone marrow-derived macrophages in a plate treated with M-CSF and RANKL.
Figure 1C:
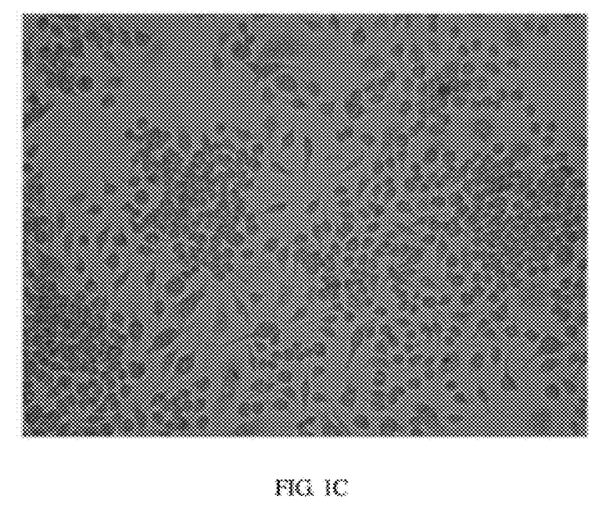
FIG. 1C is a diagram showing the results of observing murine RAW264.7 in a plate.
Figure 1D:
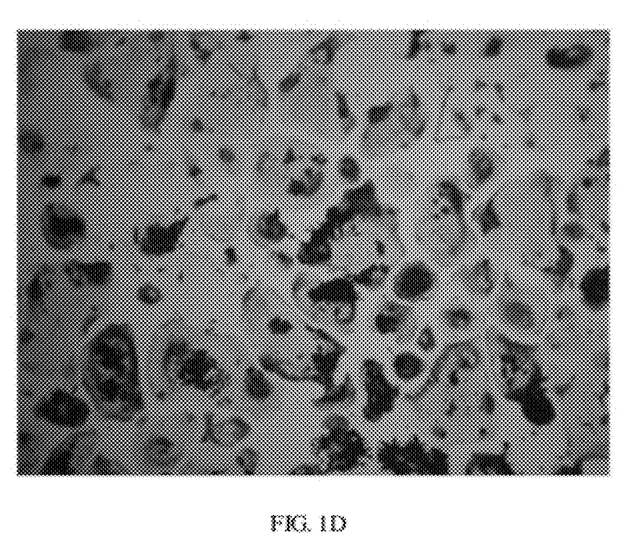
FIG. 1D is a schematic diagram showing the results of observing murine RAW264.7 in a plate treated with RANKL.

Please refer to FIG. 1A and FIG. 1B, bone marrow-derived macrophages were plated in a plate A with M-CSF (FIG. 1A) and a plate B with M-CSF and RANKL (FIG. 1B) and murine RAW264.7 were plated in a plate C (FIG. 1C) and a plate D with RANKL (FIG. 1D) separately. After a period, the growth of the osteoclast in the plate A (plate C) is different from that in the plate B (plate D). According to the abovementioned, M-CSF and RANKL secreted by the osteoblasts will promote the growth of the osteoclast. Therefore, the growth of the osteoclast cannot be seen in the plate A. In the contrast, there are a lot of osteoclasts grown in the plate B.

Figure 2A:
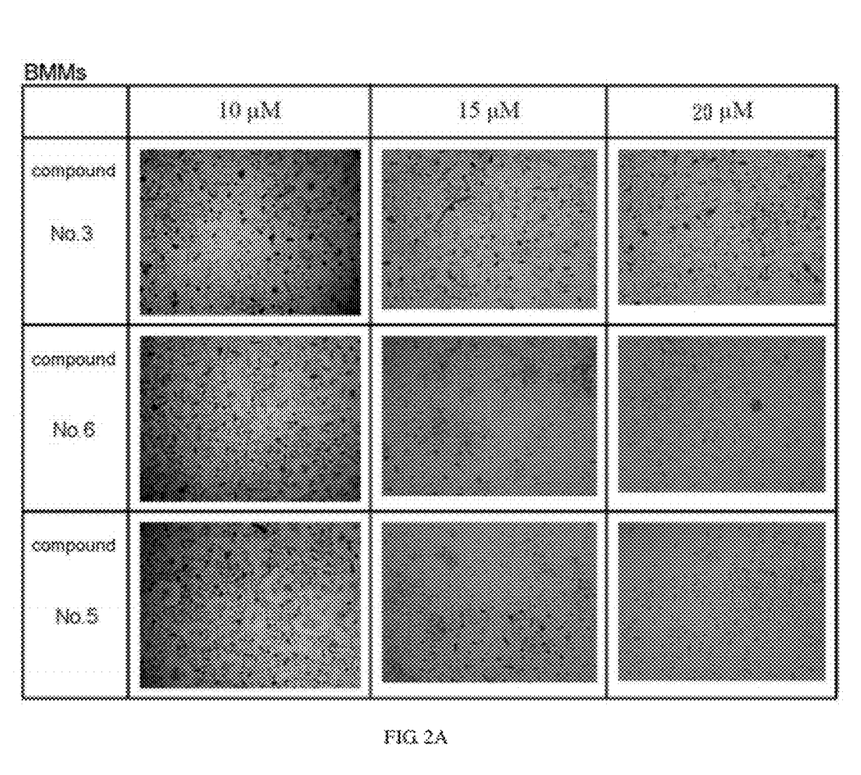
FIG. 2A is a diagram showing the results of observing bone marrow-derived macrophages in a plate containing various concentrations of the compound No. 3, No. 5 and No. 6.
Figure 2B:
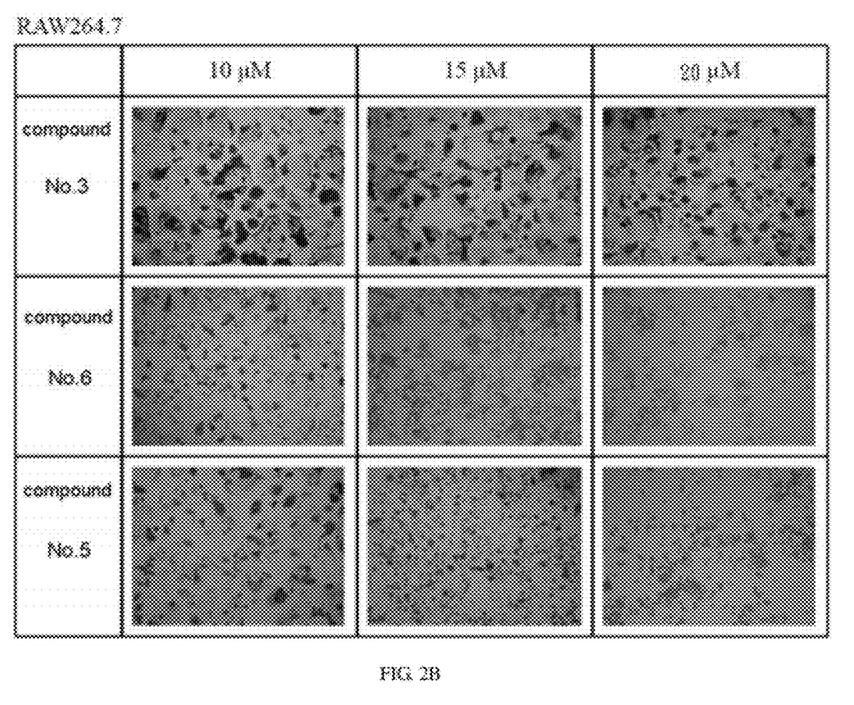
FIG. 2B is a diagram showing the results of observing murine RAW264.7 in a plate containing various concentrations of the compound No. 3, No. 5 and No. 6.

Please refer to FIGS. 2A and 2B, various concentrations of the compound No. 3, 5 and 6 were plated in different plates. FIG. 2A shows the result of the plate added with different concentration (10 nM, 15 nM and 20 nM) of the different compound (No. 3, No. 5 and No. 6) in bone marrow-derived macrophages. FIG. 2B shows the result of the plate added with different concentration (10 nM, 15 nM and 20 nM) of the different compound (No. 3, No. 5 and No. 6) in murine RAW264.7. According to the results of the abovementioned figures, it clearly shows that the compounds No. 3, 5 and 6 exactly have the effect for inhibiting osteoclasts grown. And then, the effect of inhibiting osteoclasts grown is positive proportional to the concentration of the compounds No. 3, 5 and 6.

Figure 3:
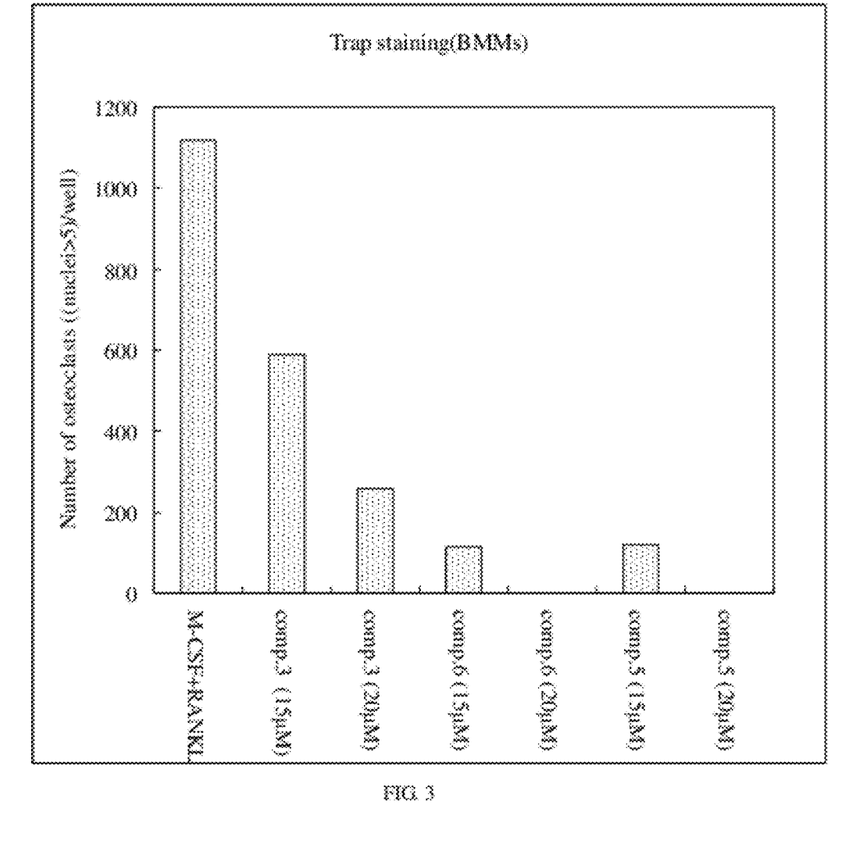
FIG. 3 is a diagram showing numbers of the osteoclasts as a function of the concentration of the compounds in bone marrow-derived macrophages.
Figure 4:
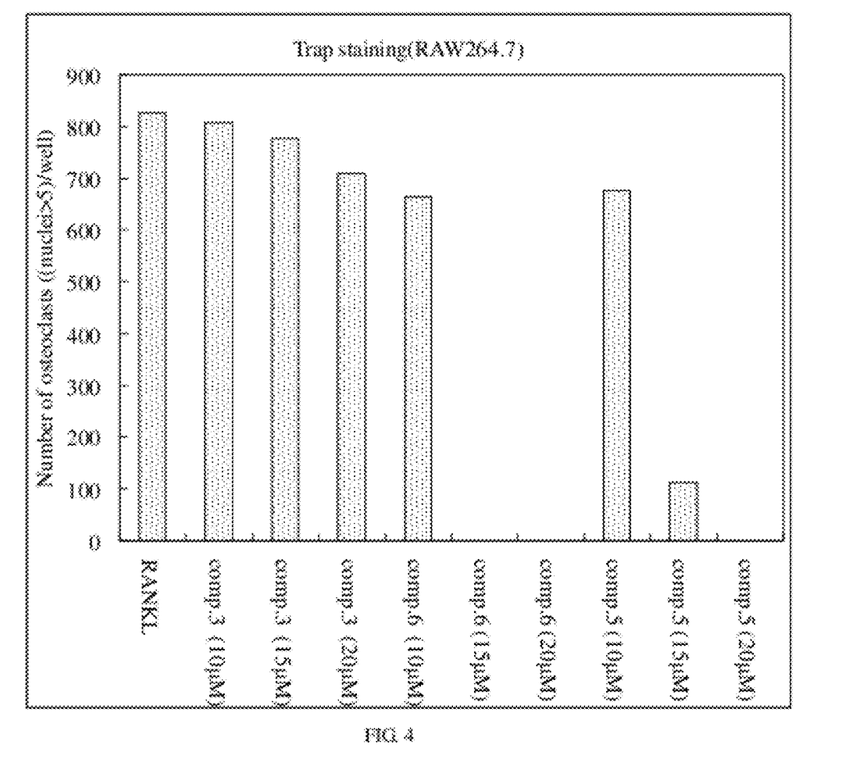
FIG. 4 is a diagram showing numbers of the osteoclasts as a function of the concentration of the compounds in murine RAW264.7.
Figure 5:
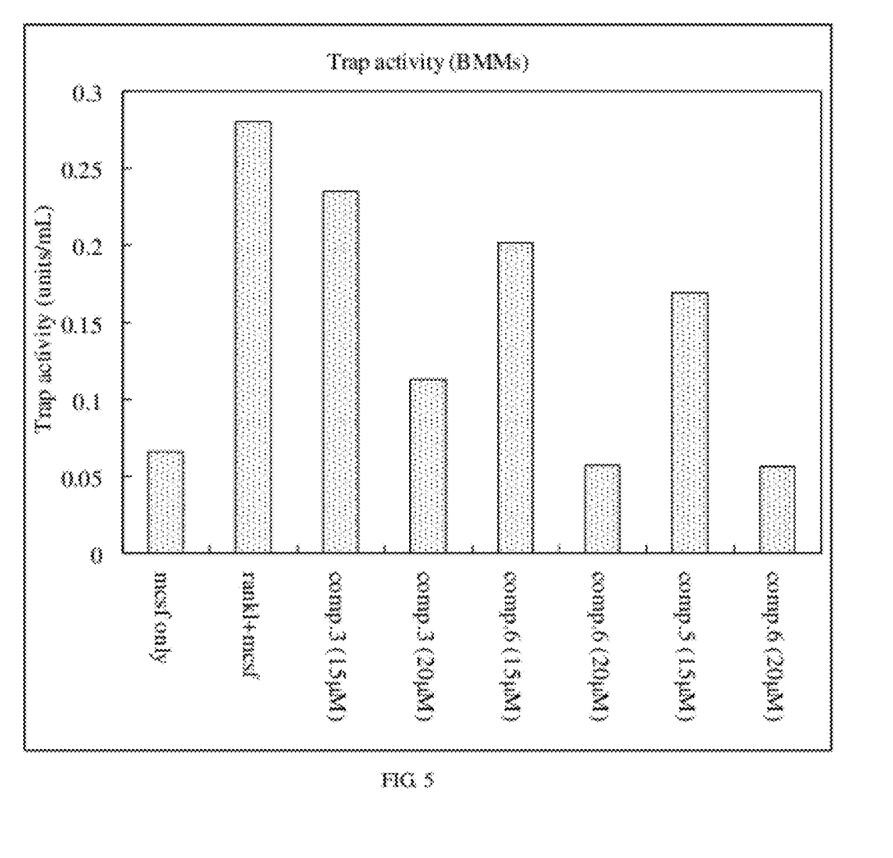
FIG. 5 is a diagram showing TRAP activities as a function of the concentration of the compounds in bone marrow-derived macrophages.

Please refer to FIG. 3 and FIG. 4, it shows the relation between the concentration of the compounds No. 3, 5, 6 and numbers of osteoclasts in two cell lines. The different concentrations of the compound No. 3, 5 and 6 can inhibit osteoclasts grown comparing to the contrast containing M-CSF and RANKL only in bone marrow-derived macrophages (RANKL only in murine RAW264.7). After dying by TRAP, the activities of the abovementioned compounds added in the abovementioned plates can be observed as shown in FIG. 5. And then, the results shown in FIG. 5 are same as those in FIG. 3. That is, the growth of the osteoclasts can be exactly inhibited when the plates are added the compounds No. 3, 5 and 6 manufactured by the method provided in the present invention.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A pharmaceutical composition for inhibiting osteoclast precursor growth comprising N-(3-ethynylphenyl)-2-hydroxybenzamide, a pharmaceutically acceptable salt, and a carrier.

2. The pharmaceutical composition according to claim 1, wherein the carrier is an excipient, a diluent, a thickener, a filler, a binder, a disintegrant, a lubricant, a oleaginous base, an non-oleaginous base, a surfactant, a suspending agent, a coagulant, an auxiliary agent, a preservative, an anti-oxidant, a stabilizer, a colorant or a flavoring.

3. The pharmaceutical composition according to claim 2, wherein the excipient comprises microcrystalline cellulose, polyvinylpyrrolidone, corn starch, modified starches, sodium starch glycolate, resin, gelatinized starches, carbohydrate, polyethylene glycol, polyvinyl alcohol, hydroxypropyl cellulose, methylcellulose, hydroxymethyl cellulose or hydroxypropyl methylcellulose.

4. The pharmaceutical composition according to claim 1, wherein the pharmaceutically acceptable salt is a physiologically acceptable with inorganic/organic acid or base.

5. The pharmaceutical composition according to claim 1, wherein the pharmaceutical composition is a powder, a grain, a liquid, a colloid or a paste.

6. The pharmaceutical composition according to claim 1, wherein the pharmaceutical composition is formulated for oral administration, transcutaneous administration, injection administration or inhalation administration.

* * * * *